United States Patent [19]

Rhee et al.

[11] Patent Number: 5,292,802
[45] Date of Patent: Mar. 8, 1994

[54] COLLAGEN-POLYMER TUBES FOR USE IN VASCULAR SURGERY

[75] Inventors: Woonza Rhee, Palo Alto; Kimberly McCullough, Hayward, both of Calif.

[73] Assignee: Collagen Corporation, Palo Alto, Calif.

[21] Appl. No.: 985,680

[22] Filed: Dec. 2, 1992

Related U.S. Application Data

[63] Continuation-in-part of Ser. No. 922,541, Jul. 30, 1992, which is a continuation-in-part of Ser. No. 433,441, Nov. 14, 1989, Pat. No. 5,162,430, which is a continuation-in-part of Ser. No. 274,071, Nov. 21, 1988, abandoned.

[51] Int. Cl.$^5$ .................... C08G 63/48; C08G 63/91
[52] U.S. Cl. .................... 525/54.1; 523/113; 424/422; 424/423
[58] Field of Search .................... 525/54.1; 523/113; 424/422, 423, 400

[56] References Cited

U.S. PATENT DOCUMENTS

| | | | |
|---|---|---|---|
| 3,619,371 | 11/1971 | Crook et al. | 525/54.1 |
| 3,788,948 | 1/1974 | Kagedal et al. | 525/54.1 |
| 3,876,501 | 4/1975 | Hanushewsky | 3/1 |
| 3,949,073 | 4/1976 | Daniels et al. | 530/356 |
| 3,960,830 | 6/1976 | Bayer et al. | 530/351 |
| 4,002,531 | 1/1977 | Royer | 435/179 |
| 4,055,635 | 10/1977 | Green et al. | 424/78 |
| 4,088,538 | 5/1978 | Schneider | 435/179 |
| 4,179,337 | 12/1979 | Davis | 435/181 |
| 4,192,021 | 3/1980 | Deibig et al. | 3/1.9 |
| 4,261,973 | 4/1981 | Lee et al. | 424/88 |
| 4,301,144 | 11/1981 | Iwashita et al. | 525/54.1 |
| 4,314,380 | 2/1982 | Miyata et al. | 530/350 |
| 4,357,274 | 11/1982 | Werner | 530/350 |
| 4,412,989 | 11/1983 | Iwashita et al. | 525/54.1 |
| 4,414,147 | 11/1983 | Klibanov et al. | 530/356 |
| 4,415,665 | 11/1983 | Mosbach et al. | 435/179 |
| 4,424,208 | 1/1984 | Wallace et al. | 514/21 |
| 4,451,568 | 5/1984 | Schneider et al. | 525/54.1 |
| 4,488,911 | 12/1984 | Luck et al. | 106/161 |
| 4,495,285 | 1/1985 | Shimizu et al. | 435/215 |
| 4,496,689 | 1/1985 | Mitra | 525/54.1 |
| 4,557,764 | 12/1985 | Chu | 106/161 |
| 4,563,350 | 1/1986 | Nathan et al. | 514/21 |
| 4,563,490 | 1/1986 | Stol et al. | 530/356 |

(List continued on next page.)

FOREIGN PATENT DOCUMENTS

| | | |
|---|---|---|
| 098110 | 1/1984 | European Pat. Off. . |
| 247860 | 12/1987 | European Pat. Off. . |
| 4227265 | 4/1990 | Japan . |
| WO84/01106 | 3/1984 | PCT Int'l Appl. . |
| WO87/04078 | 7/1987 | PCT Int'l Appl. . |

OTHER PUBLICATIONS

A. T. Viau et al. "Safety Evaluation of Free Radical Scavengers PEG-Catalase and PEG-Superoxide Dismutase," *J Free Rad in Bio & Med* (1986) 2:283-288.

(List continued on next page.)

Primary Examiner—Nathan M. Nutter
Attorney, Agent, or Firm—Karl Bozicevic

[57] ABSTRACT

Medical articles in the form of tubes are formed by covalently binding collagen to pharmaceutically pure, synthetic, hydrophilic polymers via specific types of chemical bonds to provide collagen/polymer conjugate formulations which are used to make the tubes. The collagen may be recombinantly produced human collagen or collagen extracted from any source, such as a bovine or human placental source, and purified and can be type I, type II or type III and may be fibrillar or non-fibrillar. The synthetic hydrophilic polymer may be polyethylene glycol and derivatives thereof having a weight average molecular weight over a range of from about 100 to about 20,000. The tube can be designed to incorporate other components such as liquid, pharmaceutically acceptable, carriers, and/or biologically active proteins such as growth factors or cytokines. The tubes contain large amounts of water when extruded and then may be dehydrated to form relatively solid but flexible tubes which can be easily stored. The tubes can be surgically implanted and attached to, or implanted within, a channel in a mammal for the purpose of repairing the channel. The tubes can be used to repair a wide range of different types of channels including but not limited to veins and arteries.

23 Claims, No Drawings

U.S. PATENT DOCUMENTS

| | | | |
|---|---|---|---|
| 4,582,640 | 4/1986 | Smestad et al. | 530/356 |
| 4,592,864 | 6/1986 | Miyata et al. | 530/356 |
| 4,642,117 | 2/1987 | Nguyen et al. | 623/11 |
| 4,678,468 | 7/1987 | Hiroyoshi | 623/1 |
| 4,687,820 | 8/1987 | Hou et al. | 525/54.1 |
| 4,689,399 | 8/1987 | Chu | 530/356 |
| 4,732,863 | 3/1988 | Tomasi et al. | 436/547 |
| 4,737,544 | 4/1988 | McCain et al. | 424/409 |
| 4,745,180 | 5/1988 | Moreland et al. | 530/351 |
| 4,766,106 | 8/1988 | Katre et al. | 524/12 |
| 4,828,563 | 5/1989 | Muller-Lierhern | 525/54.1 |
| 4,847,325 | 7/1989 | Shadle et al. | 525/54.1 |
| 4,935,465 | 6/1990 | Garman | 525/54.1 |
| 4,979,959 | 12/1990 | Guire | 525/54.1 |
| 5,162,430 | 11/1992 | Rhee et al. | 525/54.1 |
| 5,201,764 | 4/1993 | Kelman et al. | 525/54.1 |

OTHER PUBLICATIONS

A. T. Viau et al. "Toxicologic studies of a conjugate of asparaginase and polyethylene glycol in mice, rats, and dogs," *Am J Vet Res* (1986) 47:1398–401.

Nishida et al., "Hypouricaemic effect after oral administration in chickens of polyethlene glycol–modified uricase entrapped in liposomes," *J Pharm Pharmacol* (1984) 36:354–55.

Inada et al., "Ester Synthesis Catalyzed by Polyethylene Glycol–Modified Lipase in Benzene," *Biochem & Biophys Res Comm* (1984) 122:845–50.

Takahashi et al., "A Chemical Modification to Make Horseradish Peroxidase Soluble and Active in Benzene," *Biochem & Biophys Res Comm* (1984) 121:261–65.

Abuchowski et al, "Cancer Therapy with Chemically Modified Enzymes. I. Antitumor Properties of Polyethylene Glyco–Asparaginase Conjugates," *Cancer Biochem Biophys* (1987) 7:175–86.

J. A. M. Ramshaw et al., "Precipitation of Collagens by Polyethlene Glycols," *Anal Biochem* (1984) 141:361–65.

A. Bendich et al., "Immunological effects of native and polyethylene glycol–modified asparaginases from *Vibrio succinogenes* and *Escherichia coli* in normal and tumour–bearing mice," *Clin Exp Immunol* (1982) 48:273–78.

R. H. L. Chen et al., Properties of Two Urate Oxidases Modified by the Covalent Attachment of Poly(ethylene Glycol), *Biochim Biophys Acta* (1981) 660:293–98.

Davis et al., "Hypouricaemic Effect of Polyethyleneglycol Modified Urate Oxidase," *Lancet* (1981) 2:281–83.

P. S. Pyatak et al., "Preparation of a Polyethylene Glycol: Superoxide Dismutase Adduct, and an Examination of its Blood Circulating Life and Anti–Inflammatory Activity," *Res Com Chem Path Pharmacol* (1980) 29:113–27.

K. J. Wieder et al., "Some Properties of Polyethylene Glycol: Phenylalanine Ammonia–Lyase Adducts," *J Biol Chem (1979)* 254:12579–87.

K. V. Savoca et al., "Preparation of a Non–immunogenic Arginase by the Covalent Attachment of Polyethylene Glycol," *Biochim Biophys Acta* (1979) 578:47–53.

M. Chvapil et al., "Some Chemical and Biological Characteristics of a New Collagen–Polymer Compound Material," *J Biomed Mater Res* (1969) 3:315–332.

Lloyd et al., "Coupling of acrylic polymer and collagen by use of a water–soluble Carbodimide" *J. Polymer Sci. Chem Ed.* (1979) 17:3473–3483.

COLLAGEN-POLYMER TUBES FOR USE IN VASCULAR SURGERY

CROSS-REFERENCES

This application is a continuation-in-part of copending U.S. application Ser. No. 07/922,541 filed Jul. 30, 1992, which is a continuation-in-part of U.S. application Ser. No. 07/433,441 filed Nov. 14, 1989 (now U.S. Pat. No. 5,162,430 issued Nov. 10, 1992), which is a continuation-in-part of U.S. application Ser. No. 07/274,071 filed Nov. 21, 1988 (abandoned), all of which are incorporated herein by reference in full and to which applications we claim priority under 35 USC §120.

FIELD OF THE INVENTION

This invention relates to medical articles useful for the repair and/or augmentation of tubular channels in a patient and specifically to articles in the form of tubes comprising pharmaceutically acceptable, non-immunogenic, compositions produced by conjugating collagen to a synthetic hydrophilic polymer such as polyethylene glycol (PEG). The tubes can be produced by any means such as extrusion or molding and thereafter may be dehydrated to facilitate storage. The tubes are put in place to repair a channel such as a vein or artery in need of repair.

BACKGROUND OF THE INVENTION

Collagen is the major protein component of bone, cartilage, skin, and connective tissue in animals. Collagen in its native form is typically a rigid, rod-shaped molecule approximately 300 nm long and 1.5 nm in diameter. It is composed of three collagen polypeptides which form a tight triple helix. The collagen polypeptides are characterized by a long midsection having the repeating sequence -Gly-X-Y-, where X and Y are often proline or hydroxyproline, bounded at each end by the "telopeptide" regions, which constitute less than about 5% of the molecule. The telopeptide regions of the collagen chains are typically responsible for the crosslinking between chains, and for the immunogenicity of the protein. Collagen occurs in several "types", having differing physical properties. The most abundant types are Types I, II and III.

Collagen is typically isolated from natural sources, such as bovine hide, cartilage, or bones. Bones are usually dried, defatted, crushed, and demineralized to extract collagen, while hide and cartilage are usually minced and digested with proteolytic enzymes (other than collagenase). As collagen is resistant to most proteolytic enzymes, this procedure conveniently serves to remove most of the contaminating protein found with collagen.

Collagen may be denatured by boiling, which produces the familiar product gelatin.

Daniels et al, U.S. Pat. No. 3,949,073, disclosed the preparation of soluble collagen by dissolving tissue in aqueous acid, followed by enzymatic digestion. The resulting atelopeptide collagen is soluble, and substantially less immunogenic than unmodified collagen. It may be injected into suitable locations of a subject with a fibril-formation promoter (described as a polymerization promoter in the patent) to form fibrous collagen implants in situ, for augmenting hard or soft tissue. This material is now commercially available from Collagen Corporation (Palo Alto, Calif.) under the trademark Zyderm ® collagen implant.

Luck et al, U.S. Pat. No. 4,488,911, disclosed a method for preparing collagen in solution (CIS), wherein native collagen is extracted from animal tissue in dilute aqueous acid, followed by digestion with an enzyme such as pepsin, trypsin, or Pronase ®. The enzyme digestion removes the telopeptide portions of the collagen molecules, providing "atelopeptide" collagen in solution. The atelopeptide CIS so produced is substantially non-immunogenic, and is also substantially noncrosslinked due to loss of the primary crosslinking regions. The CIS may then be precipitated by dialysis in a moderate shear environment to produce collagen fibers which resemble native collagen fibers. The precipitated, reconstituted fibers may additionally be crosslinked using a chemical agent (for example aldehydes such as formaldehyde and glutaraldehyde), or using heat or radiation. The resulting products are suitable for use in medical implants due to their biocompatibility and reduced immunogenicity.

Wallace et al, U.S. Pat. No. 4,424,208, disclosed an improved collagen formulation suitable for use in soft tissue augmentation. Wallace's formulation comprises reconstituted fibrillar atelopeptide collagen (for example, Zyderm ® collagen) in combination with particulate, crosslinked atelopeptide collagen dispersed in an aqueous medium. The addition of particulate crosslinked collagen improves the implant's persistence, or ability to resist shrinkage following implantation.

Smestad et al, U.S. Pat. No. 4,582,640, disclosed a glutaraldehyde crosslinked atelopeptide CIS preparation (GAX) suitable for use in medical implants. The collagen is crosslinked under conditions favoring intrafiber bonding rather than interfiber bonding, and provides a product with higher persistence than non-crosslinked atelopeptide collagen, and is commercially available from Collagen Corporation under the trademark Zyplast ® Implant.

Nguyen et al, U.S. Pat. No. 4,642,117, disclosed a method for reducing the viscosity of atelopeptide CIS by mechanical shearing. Reconstituted collagen fibers are passed through a fine-mesh screen until viscosity is reduced to a practical level for injection.

Nathan et al, U.S. Pat. No. 4,563,350, disclosed osteoinductive bone repair compositions comprising an osteoinductive factor, at least 5% nonreconstituted (afibrillar) collagen, and the remainder reconstituted collagen and/or mineral powder (e.g., hydroxyapatite). CIS may be used for the nonreconstituted collagen, and Zyderm ® collagen implant (ZCI) is preferred for the reconstituted collagen component. The material is implanted in bone defects or fractures to speed ingrowth of osteoclasts and promote new bone growth.

Chu, U.S. Pat. No. 4,557,764, disclosed a "second nucleation" 60 collagen precipitate which exhibits a desirable malleability and putty-like consistency. Collagen is provided in solution (e.g., at 2–4 mg/mL), and a "first nucleation product" is precipitated by rapid titration and centrifugation. The remaining supernatant (containing the bulk of the original collagen) is then decanted and allowed to stand overnight. The precipitated second nucleation product is collected by centrifugation.

Chu, U.S. Pat. No. 4,689,399, disclosed a collagen membrane preparation, which is prepared by compressing and drying a collagen gel. The resulting product has high tensile strength.

J. A. M. Ramshaw et al, *Anal Biochem* (1984) 141:361-65, and PCT application WO87/04078 disclosed the precipitation of bovine collagen (types I, II, and III) from aqueous PEG solutions, where there is no binding between collagen and PEG.

Werner, U.S. Pat. No. 4,357,274, disclosed a method for improving the durability of sclero protein (e.g., brain meninges) by soaking the degreased tissue in $H_2O_2$ or PEG for several hours prior to lyophilizing. The resulting modified whole tissue exhibits increased persistence.

Hiroyoshi, U.S. Pat. No. 4,678,468, disclosed the preparation of polysiloxane polymers having an interpenetrating network of water-soluble polymer dispersed within. The water-soluble polymer may be a collagen derivative, and the polymer may additionally include heparin. The polymers are shaped into artificial blood vessel grafts, and are designed to prevent clotting.

Other patents disclose the use of collagen preparations with bone fragments or minerals, For example, Miyata et al, U.S. Pat. No. 4,314,380 disclosed a bone implant prepared by baking animal bone segments, and soaking the baked segments in a solution of atelopeptide collagen. Deibig et al, U.S. Pat. No. 4,192,021 disclosed an implant material which comprises powdered calcium phosphate in a pasty formulation with a biodegradable polymer (which may be collagen). Commonly-owned copending US Patent application Ser. No. 855,004, filed 22 Apr. 1986, disclosed a particularly effective bone repair material comprising autologous bone marrow, collagen, and particulate calcium phosphate in a solid, malleable formulation.

There are several references in the art to proteins modified by covalent conjugation to polymers, to alter the solubility, antigenicity and biological clearance of the protein. For example, U.S. Pat. No. 4,261,973 disclosed the conjugation of several allergans to PEG or PPG (polypropylene glycol) to reduce, the proteins' immunogenicity. U.S. Pat. No. 4,301,144 disclosed the conjugation of hemoglobin with PEG and other polymers to increase the protein's oxygen carrying capability. EPO 98,110 disclosed coupling an enzyme or interferon to a polyoxyethylene-polyoxypropylene (POE-POP) block polymer increases the protein's halflife in serum. U.S. Pat. No. 4,179,337 disclosed conjugating hydrophilic enzymes and insulin to PEG or PPG to reduce immunogenicity. Davis et al, *Lancet* (1981) 2:281-83 disclosed the enzyme uricase modified by conjugation with PEG to provide uric acid metabolism in serum having a long halflife and low immunogenicity. Nishida et al, *J Pharm Pharmacol* (1984) 36:354-55 disclosed PEG-uricase conjugates administered orally to chickens, demonstrating decreased serum levels of uric acid. Inada et al, *Biochem & Biophys Res Comm* (1984) 122:845-50 disclosed lipoprotein lipase conjugation with PEG to render it soluble in organic solvents. Takahashi et al, *Biochem & Biophys Res Comm* (1984) 121:261-65 disclosed HRP conjugated with PEG to render the enzyme soluble in benzene. Abuchowski et al, *Cancer Biochem Biophys* (1984) 7:175-86 disclosed that enzymes such as asparaginase, catalase, uricase, arginase, trypsin, superoxide dismutase, adenosine deaminase, phenylalanine ammonia-lyase, and the like, conjugated with PEG exhibit longer half-lives in serum and decreased immunogenicity. However, these references are essentially concerned with modifying the solubility and biological characteristics of proteins administered in low concentrations in aqueous solution.

M. Chvapil et al, *J Biomed Mater Res* (1969) 3:315-32 disclosed a composition prepared from collagen sponge and a crosslinked ethylene glycol monomethacrylate-ethylene glycol dimethacrylate hydrogel. The collagen sponge was prepared by lyophilizing an aqueous mixture of bovine hide collagen and methylglyoxal (a tanning agent). The sponge-hydrogel composition was prepared by polymerizing ethylene glycol monomethacrylate and ethylene glycol dimethacrylate in the sponge.

SUMMARY OF THE INVENTION

Medical articles in the form of extruded elongated hollow cylinders or tubes are produced by a variety of means including molding or forming a solid cylinder and removing the center. The composition used to form a tube is a pharmaceutically acceptable non-immunogenic composition formed by covalently binding atelopeptide collagen to pharmaceutically pure, synthetic, hydrophilic polymers via specific types of chemical bonds to provide collagen/polymer conjugates. Any type of collagen can be used including recombinantly produced human collagen and extracted and purified collagen including atelopeptide collagen which can be type I, type II or type III collagen. The collagen can be extracted from various sources such as bovine hide and human placenta and may be fibrillar or non-fibrillar. The synthetic hydrophilic polymer may be polyethylene glycol and derivatives thereof having a weight average molecular weight over a range of from about 100 to about 20,000. The compositions may include other components such as biologically active proteins such as cytokines which may be incorporated in the tubes. The collagen-polymer conjugates of the invention generally contain large amounts of water when formed. The extruded tubes may be dehydrated, resulting in a flexible tube which can be readily stored. The rehydrated flexible tubes can be surgically placed in or connected to the channel of a living being for the purpose of repair or augmentation. When rehydrated, the tube will rehydrate and expand in size five fold or more from its dehydrated size.

A primary object of the invention is to provide dehydrated hollow cylinders or tubes comprised of collagen-polymer conjugates formed by covalently binding polymers such as polyethylene glycol to collagen.

Another object of the invention is to provide a method of repairing and/or augmenting a channel in a patient by surgically implanting a tube comprised of collagen-polymer conjugates.

An advantage of the present invention is that the collagen-polymer conjugates have a high degree of stability over long periods of time under physiological conditions.

Still another advantage of the invention is that the tubes can be produced in a variety of sizes (diameters, inside and out, and length) and thereby readily used to repair all types and sizes of channels.

A feature of the invention is that the conjugates can be formed using a range of different molecular weight polymers in order to adjust physical characteristics of the tubes such as flexibility and amount of expansion on rehydration.

Another feature of the invention is that the tubes may be formed having a variety of different cross-sections including circular, oval, and rectangular as well as a variety of different shapes such as straight tubes and ribbed surfaces, all of which may be varied depending on the intended end use.

Another advantage of the present invention is that the tubes comprised of collagen-polymer conjugate compositions generate a decreased immune reaction as compared with articles comprised of conventional pharmaceutically acceptable collagen compositions and collagen compositions crosslinked by other means, such as heat, irradiation, or glutaraldehyde treatment.

Other advantages and features of the present invention is that the tubes are compact and easy to handle in their dehydrated form, allowing them to be readily stored, transported and inserted into a patient for repair and/or augmentation of a channel such as a vein or artery.

Other features of the present invention include the ability to formulate the compositions used to form the tubes with pharmaceutically active molecules such as cytokines or growth factors in order to improve the activity and available half-life of such cytokines under physiological conditions.

Another feature of the present invention is that the collagen may be bound to the polymer by means of a covalent ether linkage for long-term stability, or by an ester linkage when it is desirable to have the tube degrade over time.

These and other objects, advantages and features of the present invention will become apparent to those persons skilled in the art upon reading the details of the structure, synthesis, and usage of the tubes comprised of collagen-polymer conjugates as more fully set forth below, reference being made to the specific examples and formulations forming a part hereof.

DETAILED DESCRIPTION OF PREFERRED EMBODIMENTS OF THE INVENTION

Before the tubes comprised of collagen-polymer conjugates and processes for making and using such are described, it is to be understood that this invention is not limited to the particular tubes, conjugates, processes or methods described as such may, of course, vary. It is also to be understood that the terminology used herein is for the purpose of describing particular embodiments only, and is not intended to be limiting as the scope of the present invention will be limited only by the appended claims.

It must be noted that, as used in this specification and the appended claims, the singular forms "a", "an" and "the" include plural referents unless the context clearly dictates otherwise. Thus, for example, reference to "a tube" includes one or more tubes, reference to "an amino group" includes one or more different types of amino groups known to those skilled in the art and reference to "the collagen" includes mixtures of different types of collagen and so forth.

Unless defined otherwise, all technical and scientific terms used herein have the same meaning as commonly understood by one of ordinary skill in the art to which this invention belongs. Although any methods and materials similar or equivalent to those described herein may be useful in the practice or testing of the present invention, preferred methods and materials are described below. All publications mentioned herein are incorporated herein by reference. Further, specific terminology of particular importance to the description of the present invention is defined below.

A. Definitions

The term "collagen" as used herein refers to all forms of collagen, including those which have been recombinantly produced, extracted, processed or otherwise modified. Preferred collagens are non-immunogenic and, if extracted from animals, are treated to remove the immunogenic telopeptide regions ("atelopeptide collagen"), are soluble, and may be in the fibrillar or non-fibrillar form. Type I collagen is best suited to most applications involving bone or cartilage repair. However, other forms of collagen are also useful in the practice of the invention, and are not excluded from consideration here. Collagen crosslinked using heat, radiation, or chemical agents such as glutaraldehyde may be conjugated with polymers as described herein to form particularly rigid compositions. Collagen crosslinked using glutaraldehyde or other (nonpolymer) linking agents is referred to herein as "GAX", while collagen crosslinked using heat and/or radiation is termed "HRX." Collagen used in connection with the preferred embodiments of the invention is in a pharmaceutically pure form such that it can be incorporated into a human body for the intended purpose.

The term "synthetic hydrophilic polymer" as used herein refers to a synthetic polymer having an average molecular weight and composition which renders the polymer essentially water-soluble. Preferred polymers are highly pure or are purified to a highly pure state such that the polymer is, or is treated to become, pharmaceutically pure. Most hydrophilic polymers can be rendered water-soluble by incorporating a sufficient number of oxygen (or less frequently nitrogen) atoms available for forming hydrogen bonds in aqueous solutions. Preferred polymers are hydrophilic but not soluble. Preferred hydrophilic polymers used herein include polyethylene glycol, polyoxyethylene, polymethylene glycol, polytrimethylene glycols, polyvinylpyrrolidones, and derivatives thereof. The polymers can be linear or multiply branched and will not be substantially crosslinked. Other suitable polymers include polyoxyethylene-polyoxypropylene block polymers and copolymers. Polyoxyethylene-polyoxypropylene block polymers having an ethylene diamine nucleus (and thus having four ends) are also available and may be used in the practice of the invention. Naturally occurring and/or biologically active polymers such as proteins, starch, cellulose, heparin, and the like are expressly excluded from the scope of this definition although the invention includes polymer mixtures with naturally occurring polymers therein, i.e., the natural polymer is not used to form the basic collagen/polymer conjugate but might be mixed with or bound to the conjugate after it is formed. All suitable polymers will be non-toxic, non-inflammatory and non-immunogenic when used to form tubes, and will preferably be essentially nondegradable in vivo over a period of at least several months. The hydrophilic polymer may increase the hydrophilicity of the collagen, but does not render it water-soluble. Presently preferred hydrophilic polymers are mono-, di-, and multifunctional polyethylene glycols (PEG). Monofunctional PEG has only one reactive hydroxy group, while difunctional PEG has reactive groups at each end. Monofunctional PEG preferably has a weight average molecular weight between about 100 and about 15,000, more preferably between about 200 and about 8,000, and most preferably about 4,000. Difunctional PEG preferably has a molecular weight of about 400 to about 40,000, more preferably about 3,000 to about 10,000. Multifunctional PEG preferably has a molecular weight between about 3,000 and 100,000.

PEG can be rendered monofunctional by forming an alkylene ether at one end. The alkylene ether may be any suitable alkoxy radical having 1–6 carbon atoms, for example, methoxy, ethoxy, propoxy, 2-propoxy, butoxy, hexyloxy, and the like. Methoxy is presently preferred. Difunctional PEG is provided by allowing a reactive hydroxy group at each end of the linear molecule. The reactive groups are preferably at the ends of the polymer, but may be provided along the length thereof. Polyfunctional molecules are capable of cross-linking the compositions of the invention, and may be used to attach cytokines or growth factors to collagen which can diffuse out of the tubes.

The term "chemically conjugated" as used herein means attached through a covalent chemical bond. In the practice of the invention, a synthetic hydrophilic polymer and collagen may be chemically conjugated by using a linking radical, so that the polymer and collagen are each bound to the radical, but not directly to each other. The term "collagen-polymer" refers to collagen chemically conjugated to a synthetic hydrophilic polymer, within the meaning of this invention. Thus, "collagen-PEG" (or "PEG-collagen) denotes a composition of the invention wherein collagen is chemically conjugated to PEG. "Collagen-dPEG" refers to collagen chemically conjugated to difunctional PEG, wherein the collagen molecules are typically crosslinked. "Crosslinked collagen" refers to collagen in which collagen molecules are linked by covalent bonds with polyfunctional (including difunctional) polymers. Terms such as "GAX-dPEG" and "HRX-dPEG" indicate collagen crosslinked by both a difunctional hydrophilic polymer and a crosslinking agent such as glutaraldehyde or heat. The polymer may be "chemically conjugated" to the collagen by means of a number of different types of chemical linkages. For example, the conjugation can be via an ester or urethane linkage, but is more preferably by means of an ether linkage. An ether linkage is preferred in that it can be formed without the use of toxic chemicals and is not readily susceptible to hydrolysis in vivo.

Those of ordinary skill in the art will appreciate that synthetic polymers such as polyethylene glycol cannot be prepared practically to have exact molecular weights, and that the term "molecular weight" as used herein refers to the weight average molecular weight of a number of molecules in any given sample, as commonly used in the art. Thus, a sample of PEG 2,000 might contain a statistical mixture of polymer molecules ranging in weight from, for example, 1,500 to 2,500 daltons with one molecule differing slightly from the next over a range. Specification of a range of molecular weight indicates that the average molecular weight may be any value between the limits specified, and may include molecules outside those limits. Thus, a molecular weight range of about 800 to about 20,000 indicates an average molecular weight of at least about 800, ranging up to about 20 kDa.

The term "available lysine residue" as used herein refers to lysine side chains exposed on the outer surface of collagen molecules, which are positioned in a manner to allow reaction with activated PEG. The number of available lysine residues may be determined by reaction with sodium 2,4,6-trinitrobenzenesulfonate (TNBS).

The terms "treat" and "treatment" as used herein refer to augmentation, repair, prevention, or alleviation of defects, particularly defects due to loss or absence of all or a portion of a channel comprised of soft tissue. Additionally, "treat" and "treatment" also refer to the use of tubes which aid in the healing of damaged channels, particularly when combined with a biologically active protein coupled to the collagen-polymer composition. Accordingly, treatment of soft tissue channels includes augmentation of such channels, for example, implantation of a tube of the invention to restore normal blood flow through a portion of an artery, or as in the replacement of a defective or damaged segment of the intestines, urinary tract, or esophagus.

The terms 637 cytokine" and "growth factor" are used to describe biologically active molecules and active peptides (which may be naturally occurring or synthetic) which aid in healing or regrowth of normal tissue. The function of cytokines and growth factors is two-fold: 1) they can incite local cells to produce new collagen or tissue, or 2) they can attract cells to the site in need of correction. As such, cytokines and growth factors serve to encourage "biological anchoring" of the collagen implant within the host tissue. As previously described, the cytokines and growth factors can either be admixed with the collagen-polymer conjugate or chemically coupled to the conjugate. For example, one may incorporate cytokines such as interferons (IFN), tumor necrosis factors (TNF), interleukins, colony stimulating factors (CSFs), or growth factors such as epidermal growth factor (EGF), transforming growth factor (TGF) alpha, TGF-$\beta$ (including any combination of TGF-$\beta$s), TGF-$\beta$1, TGF-$\beta$2, platelet derived growth factor (PDGF-AA, PDGF-AB, PDGF-BB), acidic fibroblast growth factor (FGF), basic FGF, connective tissue activating peptides (CTAP), $\beta$-thromboglobulin, insulin-like growth factors, erythropoietin (EPO), nerve growth factor (NGF), bone morphogenic protein (BMP), osteogenic factors, and the like. Incorporation of cytokines, growth factors, and appropriate combinations of cytokines and growth factors can facilitate regrowth when the tubes are used in the treatment of defective or damaged channels. Furthermore, one may chemically link the cytokines and growth factors to the collagen-polymer composition by employing a suitable amount of multifunctional polymer molecules during synthesis. The cytokines may then be attached to the free polymer ends by the same method used to attach PEG to collagen, or by any other suitable method. By tethering cytokines to the outer and/or inner surface of the tubes, the amount of cytokine needed to carry out effective treatment is substantially reduced. Tubes which incorporate cytokines or growth factors may provide effective controlled-release drug delivery. By varying the chemical linkage between the collagen and the synthetic polymer, it is possible to vary the effect with respect to the release of the cytokine. For example, when an "ester" linkage is used, the linkage is more easily broken under physiological conditions, allowing for sustained release of the growth factor from the matrix. However, when an 637 ether" linkage is used, the bonds are not easily broken and the cytokine or growth factor will remain in place for longer periods of time with its active sites exposed providing a biological effect on the natural substrate for the active site of the protein. It is possible to include a mixture of conjugates with different linkages so as to obtain variations in the effect with respect to the release of the cytokine, i.e., the sustained release effect can be modified to obtain the desired rate of release.

The terms "effective amount" or "amount effective to treat" refer to the amount of composition required in order to obtain the effect desired. Thus, a "tissue growth-promoting amount" of a composition containing a cytokine refers to the amount of cytokine needed in order to stimulate tissue growth to a detectable degree. Tissue, in this context, includes connective tissue, bone, cartilage, epidermis and dermis, blood, and other tissues with particular emphasis on tissues which form channels such as veins, arteries, intestines and the like. The actual amount which is determined to be an effective amount will vary depending on factors such as the size, condition, sex and age of the patient, the type of tissue or channel, the effect desired and type of cytokine, and can be more readily determined by the caregiver.

The term "sufficient amount" as used herein is applied to the amount of carrier used in combination with the collagen-polymer conjugates used in forming the tubes of the invention. A sufficient amount is that amount which, when mixed with the conjugate, renders it in the physical form desired, for example, extrudable tubes, extrudable cylinders having any desired cross-section, and so forth. Extrudable formulations may include an amount of a carrier sufficient to render the composition smoothly extrudable without significant need to interrupt the extrusion process. The amount of the carrier can be varied and adjusted depending on the size and shape and thickness of the wall of the tube being extruded. Such adjustments will be apparent to those skilled in the art upon reading this disclosure.

The term "suitable fibrous material", as used herein, refers to a fibrous material which is substantially insoluble in water, non-immunogenic, biocompatible, and capable of being combined and/or integrated or connected to the tubes of the invention. The fibrous material may comprise a variety of materials having these characteristics and are combined with the tubes in order to form and/or provide structural integrity for the tubes used to repair and/or augment channels. For example, tubes may be extruded with a tubular piece of fabric or threads embedded in the wall of the tube in order to provide structural integrity to the tube. Thus, the "suitable fibrous material" is useful in forming the different embodiments of the invention.

The term "in situ" as used herein means at the site of administration. Dehydrated or partially rehydrated tubes may be surgically implanted inside, outside or attached to a channel to be repaired or augmented, and allowed to fully hydrate and expand at the site of injection. Suitable sites will generally be veins, arteries, intestines and the like.

The term "aqueous mixture" of collagen includes liquid solutions, suspensions, dispersions, colloids, and the like containing collagen and water.

The term "dehydrated" means the tube is air-dried or lyophilized to remove substantially all unbound water.

The term "flexible" means the dehydrated tube can be easily bent 90° or more without breaking.

The term "NFC cartilage" as used herein refers to a composition of the invention which resembles cartilage in physical consistency. NFC cartilage is prepared from nonfibrillar collagen (e.g., collagen in solution) and is crosslinked with a hydrophilic polymer, especially using dPEG. As an artifact of the production process or by design, NFC cartilage may contain about 0-20% fibrillar collagen. NFC cartilage is generally prepared by adding dPEG in acidic solution to an acidic solution of collagen, and allowing conjugation to occur prior to neutralization. The term "NFC-FC cartilage" refers to a composition similar to NFC cartilage, wherein the percentage of fibrillar collagen is about 20-80%. NFC-FC cartilage is generally prepared by adding dPEG in a neutralizing buffer to an acidic solution of collagen. The neutralizing buffer causes collagen fibril formation during the conjugation process. Similarly, "FC cartilage" refers to a composition of the invention which is prepared from fibrillar collagen and a difunctional hydrophilic polymer. FC cartilage may generally be prepared using dPEG and fibrillar collagen in neutral solutions/suspensions.

B. General Method

B.1 Preparation: Extruded Tubes

A variety of different collagen-polymer conjugate formulations can be prepared as described below. The formulations are extruded through any suitable orifice including the nozzle of an extruding device using extrusion technology known to those skilled in the art. The tubes of the invention may be extruded in any desired shape or size including elongated hollow tubes and solid elongated cylinders. When the tube to be formed is initially extruded as a solid cylinder the center of the cylinder must be removed or perforated in some manner so as to form the hollow opening of the tube. This can be done in a variety of ways. For example, a solid tube may be extruded from a wide bore needle as per Example 8. Crosslinking will proceed from the external diameter inward. After a given period of time, the crosslinking will form a tubular wall and the cylinder can be squeezed to force out the uncrosslinked material in the center, thereby forming a hollow tube from a cylinder. Alternatively, the solid cylinder can be extruded with a smaller diameter cylindrical object inside. After extrusion, the smaller object is removed leaving the opening which is the center of a hollow tube. A solid cylinder is extruded with a smaller diameter cylindrical object contained therein. It is preferable to coat the surface of the smaller diameter cylindrical object with a nonstick coating material such as a silicone or a polyfluorocarbon compound. Further, the surface of the cylindrical object should be kept extremely smooth to facilitate removal.

Tubes of the invention are generally produced with a smooth outer and inner surface. However, it is possible to produce the tubes so that the outer and/or inner surface have any desired shape, such as an undulated surface. Producing the tubes so that the surface and/or the entire cylinder wall is undulated, it is possible to obtain a tube which readily increases or decreases in length by stretching or contracting the undulations of the tubular wall. Although the tubular walls are generally solid, it is possible to produce the tubes of the invention with openings therein. Such openings can be provided for a variety of purposes, including the attachment of other tubes.

The extruded tubes or cylinders are generally circular in cross-section but may have any cross-sectional shape including oval, square, triangular, hexagonal, etc. The tubes or cylinders may be extruded with a tubular piece of material or thread of cotton, Dacron, nylon or like material embedded therein to add to the strength of the tube. The tube can be extruded in any length (e.g., 1 cm to 100 m) and may have an external diameter in the range of about 0.25 mm to 5 cm.

In accordance with another method of production, the tubes are produced by mixing a synthetic hydrophilic polymer with collagen and, within a relatively short period of time (preferably less than 5 minutes), injecting that material into a tube-shaped mold. After the molded tube is given time to set via crosslinking, the tube is removed from the cast.

In a preferred embodiment, a pharmaceutically acceptable collagen such as ZYDERM ®I Collagen or ZYDERM ®II Collagen is mixed with an essentially equal weight amount of difunctional S-PEG followed immediately by casting the mixture into a tube-shaped mold. The mixture is allowed to gel or polymerize, thereby forming the covalent bonds between the polymer and the collagen.

Tubes may be produced by mixing commercially available collagen with difunctional S-PEG in a PBS solution for one to two minutes. After mixing the collagen and polymer together, the mixture can be subjected to a variety of different processing procedures in order to manufacture the tubes of the invention. In accordance with one method, the components are thoroughly mixed together and then placed within a syringe and injected from a wide-gauge needle of a syringe having a diameter of about 0.5 cm. The material is injected into a dilute solution containing about 10% difunctionally activated S-PEG having a temperature in the range of about 35°–40° C. The material is allowed to polymerize or crosslink within the solution for 20–30 minutes. Thereafter, the solid cylinder of material is removed from the solution and pressure is applied at one end and the pressure is moved continuously towards the other end of the cylinder. This pressure causes unpolymerized material contained within the solid cylinder to be squeezed out of the solid cylinder leaving a hollow opening, thus forming a tube. The tube can be dried by attaching both ends of the tube to supports and carrying out air drying.

In accordance with another method, after the collagen and polymer are mixed thoroughly together, the material is injected into a Teflon ® coated mold and the ends of the mold are sealed off to prevent desiccation and the tube is incubated at a temperature in the range of 35°–40° C. for approximately 12 hours to allow polymerization to be completed thereby forming covalent bonds between the collagen and the hydrophilic polymer. Thereafter, the polymerized tube can be removed from the mold and the ends of the tube clamped so that the tube is freely suspended in air. The tube may be allowed to dry and the dry tube should be substantially straight and fairly stiff yet flexible.

In yet another embodiment, the collagen-polymer solution is injected into the space between two TFE tubes of different diameters which are placed inside one another to produce a very thin-walled tube which is especially useful as a nerve graft tube.

It will be recognized by those skilled in the art that certain technical modifications will be necessary in order to optimize parameters useful in making tubes on a commercial scale. However, the details of such can be readily deduced by those skilled in the art based on the disclosure provided herein. To provide assistance in connection with optimizing various parameters, the following information is provided. This information was found to be useful in connection with producing the tubes on a laboratory useful scale.

First, the total processing time from the mixing of the collagen with the polymer should be kept at 5 minutes or less when the temperature is within the range of about 18° C. to 25° C. (room temperature) in order to avoid substantial crosslinking prior to extrusion or casting of the material and, if applicable, removal of the center of a cylinder to form a tube. Thus, the polymer and collagen should be mixed thoroughly together and extruded in the form of a tube or cylinder or injected into a tube-shaped cast within 5 minutes. If additional processing time is required the temperature can be reduced in order to reduce the rate of the crosslinking reaction.

When the mixture of polymer and collagen is cast into a tube-shaped cast it is preferable to use a cast having its internal surface coated with a wettable, non-stick, material which is designed to reduce friction and/or sticking such as silicone, and polyfluorocarbons such as a Teflon ® coating. If the cast is small in length and/or the bore of the tubing is large, and the center hole of the tube to be formed is created by an elongated cord extruded into the cast with the material, the tube with the cord (preferably rigid) still present may be extruded out of the cast using hydraulic or air pressure. If extrusion is not possible using pressure or other cast design shapes are used, the cast can be cut. Since cutting the cast may be necessary, it is desirable to use a cast design which includes perforations along the axial line of the tubing. The perforations may extend from the outside wall to the center cord of the casting at some places and not extend into the internal surface diameter of the cast at other places.

As indicated above, it is possible to use fibrillar or nonfibrillar collagen to form the tubes of the invention. However, fibrillar collagen is preferred. When the mixture of collagen and polymer is injected into a narrow bore cast or tubing (which will have its center removed later) prior to gelation or extruded from the orifice of an extrusion device, the fibers tend to orient along the axis of the tubing. This orientation is believed to impart additional tensile strength to the dried tubes. The size of the orifice of the extrusion device and/or the internal diameter of the tube-shaped cast will dictate the maximum diameter of the tube being produced. However, the tube tends to shrink substantially upon drying and such should be taken into consideration with respect to producing tubes of desired thickness, length and strength.

Prior to casting or extrusion from the orifice of an extrusion device it is important to remove any air bubbles from the mixture, i.e., carry out de-aeration. If air bubbles are trapped in the mixture, the bubbles will appear in the tube as breaks or weakened portions. In order to increase strength, it is also desirable to wash the gel after crosslinking occurs in order to remove dissolved salts and unreacted components.

After a tube is formed and polymerization has been completed, the tube may be dried. Drying can take place in a variety of different ways. For example, the tube can be placed on a flat surface and exposed to the air and/or heat. Such a procedure tends to result in the flattening of the tube on the surface which the tube is placed on. The upper surface may also be flat resulting in a deflated tube shape. When the tube is dried with one end clamped, and the other end freely hanging the freely hanging end dries randomly. Further, there is considerable overall shrinkage in the length of the tube and the final dried product is generally not straight. The free end is often jagged and wavy but becomes straighter towards the attached end. Overall, such tubes are weak and easily break. If both ends of the tube are clamped, the tube tends to dry radially and not axially which results in predictable, controlled drying. Further, the length of the tube is substantially maintained and the resulting tube is substantially straight. A similar effect can be obtained by attaching one end of the tube and allowing the other end to hang downward and attaching a small weight at the hanging end.

In general, the tube shape is preferably straight. However, coils or helixes can be produced by wrapping the tube around a small diameter rod and allowing the tube to dry. Such a procedure will result in a spring-like material which has a certain degree of resilience. Bent-shaped tubes can be made by drying the tube while holding it at the desired angle. The angle will remain in the tube when rehydrated.

It is possible to carry out a partial drying of the tube by hanging the tube from a support, and after partial drying occurs, place the partially dried tube on a drying support which is inserted into the internal diameter of the tube. By inserting an object inside the tube, it is possible to change the shape of the tube upon drying. Undulated surfaces can be created by placing a straight tube, while still wet, on a straight support, then compressing the walls of the tube along the length of the support such that the compressed tube is approximately one-half the length of the original straight tube, thereby creating undulations, or ribs, in the surface of the tube. If dried in this conformation, the walls of the tube will retain the ribbed shape when later rehydrated. The ribs, or undulations, impart additional strength, flexibility and elasticity to the tube. Further, a partially flexible object, having a helical shape, can be inserted into the internal diameter of the tube in order to create a helical tube. Other angles and bent tubular shapes can be created in this manner.

Conjugates

To form the conjugates used to make the tubes of the invention collagen must be chemically bound to a synthetic hydrophilic polymer. This can be carried out in a variety of ways. In accordance with the preferred method, the synthetic hydrophilic polymer is activated and then reacted with the collagen. Alternatively, the hydroxyl or amino groups present on the collagen can be activated and the activated groups will react with the polymer to form the conjugate. In accordance with a less preferred method, a linking group with activated hydroxyl or amino groups thereon can be combined with the polymer and collagen in a manner so as to concurrently react with both the polymer and collagen forming the conjugate. Other methods of forming the conjugates will become apparent to those skilled in the art upon reading this disclosure. Since the conjugates of the invention are to be used in the human body it is important that all of the components, including the polymer, collagen, and linking group, if used form a conjugate that is unlikely to be rejected by the body. Accordingly, toxic and/or immunoreactive components are not preferred as starting materials. Some preferred starting materials and methods of forming conjugates are described further below.

Although different hydrophilic synthetic polymers can be used in connection with forming the conjugate, such polymers must be biocompatible, relatively insoluble, but hydrophilic and is preferably one or more forms of polyethylene glycol (PEG), due to its known biocompatibility. Various forms of PEG are extensively used in the modification of biologically active molecules because PEG can be formulated to have a wide range of solubilities and because it lacks toxicity, antigenicity, immunogenicity, and does not typically interfere with the enzymatic activities and/or conformations of peptides. Further, PEG is generally non-biodegradable and is easily excreted from most living organisms including humans.

The first step in forming the collagen-polymer conjugates generally involves the functionalization of the PEG molecule. Various functionalized polyethylene glycols have been used effectively in fields such as protein modification (see Abuchowski et al., *Enzymes as Drugs*, John Wiley & Sons: New York, N.Y. (1981) pp. 367–383; and Dreborg et al., *Crit. Rev. Therap. Drug Carrier Syst.* (1990) 6:315, both of which are incorporated herein by reference), peptide chemistry (see Mutter et al., *The Peptides*, Academic: New York, N.Y. 2:285–332; and Zalipsky et al., *Int. J. Peptide Protein Res.* (1987) 30:740, both of which are incorporated herein by reference), and the synthesis of polymeric drugs (see Zalipsky et al., *Eur. Polym. J.* (1983) 19:1177; and Ouchi et al., *J. Macromol. Sci. -Chem.* (1987) A24:1011, both of which are incorporated herein by reference). Various types of conjugates formed by the binding of polyethylene glycol with specific pharmaceutically active proteins have been disclosed and found to have useful medical applications in part due to the stability of such conjugates with respect to proteolytic digestion, reduced immunogenicity and longer half-lives within living organisms.

One form of polyethylene glycol which has been found to be particularly useful is monomethoxypolyethylene glycol (mPEG), which can be activated by the addition of a compound such as cyanuric chloride, then coupled to a protein (see Abuchowski et al., *J. Biol. Chem.* (1977) 252:3578, which is incorporated herein by reference). Although such methods of activating polyethylene glycol can be used in connection with the present invention, they are not particularly desirable in that the cyanuric chloride is relatively toxic and must be completely removed from any resulting product in order to provide a pharmaceutically acceptable composition.

Activated forms of PEG can be made from reactants which can be purchased commercially. One form of activated PEG which has been found to be particularly useful in connection with the present invention is mPEG-succinate-N-hydroxysuccinimide ester (SS-PEG) (see Abuchowski et al., *Cancer Biochem. Biphys.* (1984) 7:175, which is incorporated herein by reference). Activated forms of PEG such as SS-PEG react with the proteins under relatively mild conditions and produce conjugates without destroying the specific biological activity and specificity of the protein attached to the PEG. However, when such activated PEGs are reacted with proteins, they react and form linkages by means of ester bonds. Although ester linkages can be used in connection with the present invention, they are not particularly preferred in that they undergo hydrolysis when subjected to physiological conditions over extended periods of time (see Dreborg et al., *Crit. Rev. Therap. Drug Carrier Syst.* (1990) 6:315; and Ulbrich et al., *J. Makromol. Chem.* (1986) 187:1131, both of which are incorporated herein by reference).

It is possible to link PEG to proteins via urethane linkages, thereby providing a more stable attachment which is more resistant to hydrolytic digestion than the ester linkages (see Zalipsky et al., Polymeric Drug and Drug Delivery Systems, Chapter 10, "Succinimidyl Carbonates of Polyethylene Glycol" (1991) incorporated herein by reference to disclose the chemistry involved in linking various forms of PEG to specific biologically active proteins). The stability of urethane linkages has been demonstrated under physiological conditions (see Veronese et al., *Appl. Biochem. Biotechnol.* (1985) 11:141; and Larwood et al., *J. Labelled Compounds Radiopharm.* (1984) 21:603, both of which are incorporated herein by reference). Another means of attaching the PEG to a protein can be by means of a carbamate linkage (see Beauchamp et al., *Anal. Biochem.* (1983) 131:25; and Berger et al., *Blood* (1988) 71:1641, both of which are incorporated herein by reference). The carbamate linkage is created by the use of carbonyldiimidazole-activated PEG. Although such linkages have advantages, the reactions are relatively slow and may take 2 to 3 days to complete.

The various means of activating PEG described above and publications (all of which are incorporated herein by reference) cited in connection with the activation means are described in connection with linking the PEG to specific biologically active proteins and not collagen. However, the present invention now discloses that such activated PEG compounds can be used in connection with the formation of collagen-PEG conjugates. Such conjugates provide a range of improved characteristics and as such can be used to form the various compositions used in forming the tubes of the present invention. [*Polymeric Drug and Drug Delivery Systems*, Chapter 10, "Succinimidyl Carbonates of Polyethylene Glycol" (1991), incorporated herein by reference to disclose the chemistry involved in linking various forms of PEG to specific biologically active proteins.]

B.2 Specific Forms of Activated PEG.

As indicated above, the conjugates used in forming the tubes can be prepared by covalently binding a variety of different types of synthetic hydrophilic polymers to collagen. However, because the final product or conjugate obtained must have a number of required characteristics such as being extrudable from a nozzle, biocompatible and non-immunogenic, it has been found useful to use polyethylene glycol as the synthetic hydrophilic polymer. The polyethylene glycol must be modified in order to provide activated groups on one or preferably both ends of the molecule so that covalent binding can occur between the PEG and the collagen. Some specific functionalized forms of PEG are shown structurally below, as are the products obtained by reacting these functionalized forms of PEG with collagen.

The first functionalized PEG is difunctionalized PEG succinimidyl glutarate, referred to herein as (SG-PEG). The structural formula of this molecule and the reaction product obtained by reacting it with collagen is shown in Formula 1.

FORMULA 1

S-PEG: Difunctional PEG Succinimidyl Glutarate

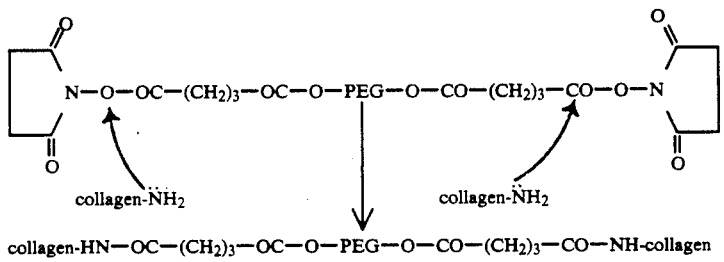

Another difunctionally activated form of PEG is referred to as PEG succinimidyl (S-PEG). The structural formula for this compound and the reaction product obtained by reacting it with collagen is shown in Formula 2. In a general structural formula for the compound of Formula 2, the subscript 3 is replaced with an "n." In the embodiment shown in Formula 1, n=3, in that there are three repeating CH$_2$ groups on each side of the PEG. The structure in Formula 2 results in a conjugate which includes an "ether" linkage which is not subject to hydrolysis. This is distinct from the first conjugate shown in Formula 1, wherein an ester linkage is provided. The ester linkage is subject to hydrolysis under physiological conditions.

FORMULA 2

S-PEG, n = 3: Difunctional PEG Succinimidyl

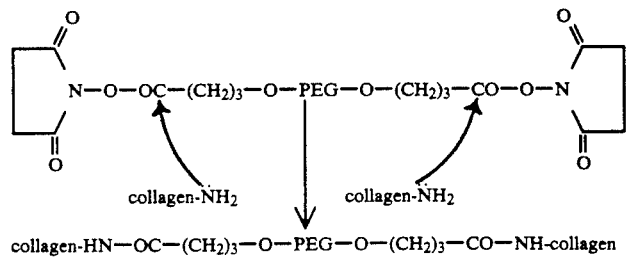

Yet another derivatized form of polyethylene glycol, wherein n=2 is shown in Formula 3, as is the conjugate formed by reacting the derivatized PEG with collagen.

FORMULA 3
S-PEG, n = 2: Difunctional PEG Succinimidyl

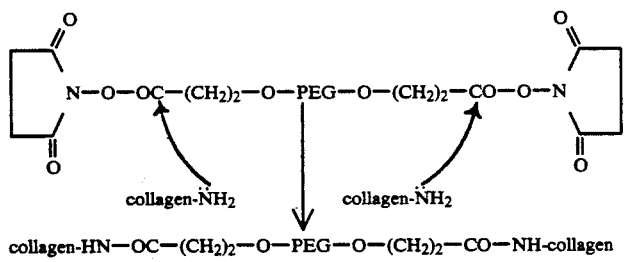

collagen-HN—OC—(CH$_2$)$_2$—O—PEG—O—(CH$_2$)$_2$—CO—NH-collagen

Another preferred embodiment of the invention similar to the compounds of Formula 2 and Formula 3, is provided when n=1. The structural formula and resulting conjugate are shown in Formula 4. It is noted that the conjugate includes both an ether and a peptide linkage. These linkages are stable under physiological conditions.

FORMULA 4
S-PEG, n = 1: Difunctional PEG Succinimidyl

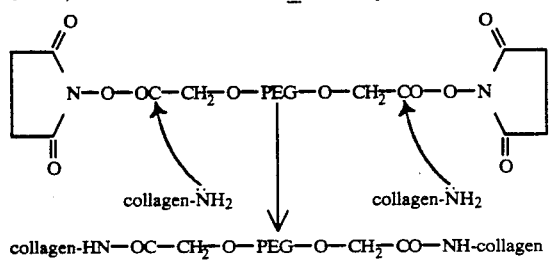

collagen-HN—OC—CH$_2$—O—PEG—O—CH$_2$—CO—NH-collagen

Yet another derivatized form of PEG is provided when n=0. The difunctionalized form is referred to as PEG succinimidyl carbonate (SC-PEG). The structural formula of this compound and the conjugate formed by reacting SC-PEG with collagen is shown in Formula 5. Although this conjugate includes a urethane linkage, the conjugate has been found not to have a high degree of stability under physiological conditions. The instability can be a desirable characteristic when the tubes are used in a situation where it is desirable that they dissolve over time.

FORMULA 5
SC-PEG, n = 0: Difunctional PEG Succinimidyl Carbonate

-continued
FORMULA 5

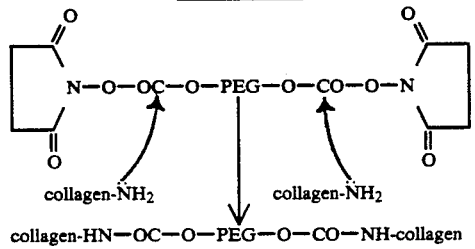

collagen-HN—OC—O—PEG—O—CO—NH-collagen

All of the derivatives depicted in Formulas 1-5 involve the inclusion of the succinimidyl group. However, different activating groups can be attached to one or both ends of the PEG. For example, the PEG can be derivatized to form difunctional PEG propion aldehyde (A-PEG), which is shown in Formula 6, as is the conjugate formed by the reaction of A-PEG with collagen.

FORMULA 6
A-PEG: Difunctional PEG Propion Aldehyde

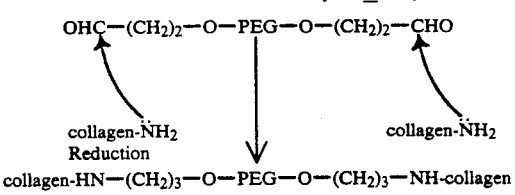

collagen-HN—(CH$_2$)$_3$—O—PEG—O—(CH$_2$)$_3$—NH-collagen

Yet another functionalized form of polyethylene glycol is difunctional PEG glycidyl ether (E-PEG), which is shown in Formula 7, as is the conjugate formed by reacting such with collagen.

FORMULA 7
E-PEG: Difunctional PEG Glycidyl Ether

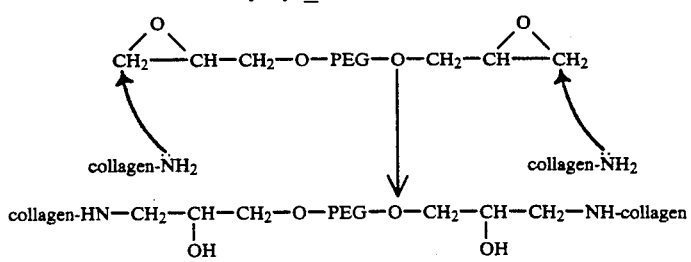

The conjugates formed using the functionalized forms of PEG vary depending on the functionalized form of PEG which is used in the reaction. Furthermore, the final product can be varied with respect to its characteristics by changing the molecular weight of the PEG. In general, the stability of the conjugate is improved by eliminating any ester linkages between the PEG and the collagen and including ether and/or urethane linkages. These stable linkages are generally used to form tubes to replace or augment a channel. When the tubes are used as a temporary repair unit for a damaged channel, it may be desirable to include the weaker ester linkages so that the linkages are gradually broken by hydrolysis under physiological conditions, breaking apart the tube as it may be replaced by host tissue, or as it degrades, and releasing a component held therein, such as a growth factor. By varying the chemical structure of the linkage, the rate of sustained release can be varied.

Polyfunctional polymers may also be used to crosslink collagen molecules to other proteins (e.g., glycosaminoglycans, chondroitin sulfates, fibronectin, and the like), particularly growth factors, for compositions particularly suited for use in wound healing, osteogenesis, and immune modulation. Such tethering of cytokines to collagen molecules provides an effective slow-release drug delivery system.

Suitable collagens include all types of pharmaceutically useful collagen, preferably types I, II and III. Collagens may be soluble (for example, commercially available Vitrogen® 100 collagen-in-solution), and may or may not have the telopeptide regions. Preferably, the collagen will be reconstituted fibrillar atelopeptide collagen, for example Zyderm® collagen implant (ZCI) or atelopeptide collagen in solution (CIS). Various forms of collagen are available commercially, or may be prepared by the processes described in, for example, U.S. Pat. Nos. 3,949,073; 4,488,911; 4,424,208; 4,582,640; 4,642,117; 4,557,764; and 4,689,399, all incorporated herein by reference. Fibrillar, atelopeptide, reconstituted collagen is preferred in order to form tubes used for the repair or augmentation of channels.

Compositions used in forming the tubes of the invention comprise collagen chemically conjugated to a selected synthetic hydrophilic polymer or polymers. Collagen contains a number of available amino and hydroxy groups which may be used to bind the synthetic hydrophilic polymer. The polymer may be bound using a "linking group", as the native hydroxy or amino groups in collagen and in the polymer frequently require activation before they can be linked. For example, one may employ compounds such as dicarboxylic anhydrides (e.g., glutaric or succinic anhydride) to form a polymer derivative (e.g., succinate), which may then be activated by esterification with a convenient leaving group, for example, N-hydroxysuccinimide, N,N'-disuccinimidyl oxalate, N,N'-disuccinimidyl carbonate, and the like. See also Davis, U.S. Pat. No. 4,179,337 for additional linking groups. Presently preferred dicarboxylic anhydrides that are used to form polymer-glutarate compositions include glutaric anhydride, adipic anhydride, 1,8-naphthalene dicarboxylic anhydride, and 1,4,5,8-naphthalenetetracarboxylic dianhydride. The polymer thus activated is then allowed to react with the collagen, forming a collagen-polymer composition used to make the tubes.

Conjugates with Ester Linkages

In one embodiment, a pharmaceutically pure form of monomethylpolyethylene glycol (mPEG) (mw 5,000) is reacted with glutaric anhydride (pure form) to create mPEG glutarate. The glutarate derivative is then reacted with N-hydroxysuccinimide to form a succinimidyl monomethylpolyethylene glycol glutarate. The succinimidyl ester (mPEG*, denoting the activated PEG intermediate) is then capable of reacting with free amino groups present on collagen (lysine residues) to form a collagen-PEG conjugate wherein one end of the PEG molecule is free or nonbound. Other polymers may be substituted for the monomethyl PEG, as described above. Similarly, the coupling reaction may be carried out using any known method for derivatizing proteins and synthetic polymers. The number of available lysines conjugated may vary from a single residue to 100% of the lysines, preferably 10-50%, and more preferably 20-30%. The number of reactive lysine residues may be determined by standard methods, for example by reaction with TNBS.

The resulting product is a smooth, pliable, rubbery mass having a shiny appearance. It may be wetted, but is not water-soluble. It may be formulated as a suspension at any convenient concentration, preferably about 30-65 mg/mL, and may be extruded through a nozzle to form a tube. The consistency of the formulation may be adjusted by varying the amount of liquid used.

Conjuqate and Growth Factors

Tubes can be formed using compositions containing growth factors such as EGF and TGF-$\beta$. The extrudable compositions are prepared by mixing an appropriate amount of the growth factor into the conjugate composition, or by incorporating the growth factor into the collagen prior to treatment with activated PEG. By employing an appropriate amount of difunctional PEG, a degree of crosslinking may be established, along with molecules consisting of collagen linked to a cytokine by a synthetic hydrophilic polymer. Preferably, the cytokine is first reacted with a molar excess of dPEG* in a dilute solution over a 3 to 4 hour period. The cytokine is preferably provided at a concentration of about 1 $\mu$g/mL to about 5 mg/mL, while the dPEG* is preferably added to a final concentration providing a 30 to 50-fold molar excess. The resulting conjugated cytokine is then added to an aqueous collagen mixture (about 1 to about 60 mg/mL) at pH 7-8 and allowed to react further. The resulting composition is allowed to stand overnight at ambient temperature.

B.2 Use and Administration:

Tubes of the invention can be used to repair, augment or replace a variety of different channels within a living being. The tubes are suitable for the repair and replacement of veins or arteries within the cardiovascular system. The tubes can be produced in a variety of different diameters and lengths in order to precisely match the size and shape of the vein or artery being replaced or augmented. In certain situations, it is desirable to merely repair a given vein or artery. In such situations, the tubes of the invention are used as a bandage or coating around the artery during the healing or repair process.

In addition, the tubes may be used as stents to prevent damaged blood vessels from collapsing and to divert the flow of blood from the site of an aneurysm. As such, the tubes are implanted directly within the damaged vessel, usually via catheter.

In addition to being used to repair, augment or replace veins or arteries, the tubes of the invention can be used to repair, replace or augment channels such as the intestines, including the small and/or large intestines, portions of the esophagus or trachea, urethra, fallopian tubes, vas deferens, eustachian tubes, and/or virtually any channel within a living being, and specifically a channel of a human used to transport fluids or material from one location to another within the body.

The tubes can be put in position by any appropriate means, including manually being placed in position by surgical means and attached, e.g., by sutures, tissue adhesives, or surgical staples. In certain situations, it is possible to implant the tubes and lock the tube into position by placing the tube over a catheter and inserting the catheter into the tube and positioning the tube within the channel by moving the catheter.

In that the tubes of the invention tend to expand in size upon hydration, it is generally preferable to store the tubes in a dehydrated form but to hydrate the tubes completely prior to putting the tubes in place within a human being. By carrying out rehydration, the final size of the tube to be inserted can be precisely determined. However, as explained below, it is possible to insert the tubes in a dehydrated form.

The tubes may be inserted in a dehydrated form and slowly hydrate and expand 5-fold or more in situ due to the presence of body fluids. However, the speed of hydration can be increased by injecting an aqueous solution into and around the tube. The aqueous solution may be a saline solution or other solution containing salts in concentrations which match the surrounding environment—generally that of human tissue.

The tubes of the invention can also be used to aid in the repair of other tissues such as nerves, tendons or muscles. When the tubes are used in this manner, they are put in place around a damaged piece of tissue such as a severed tendon, muscle, or ligament and then sewn into place. The damaged tissue is sewed together and the surrounding tube acts as a bandage while providing additional structural support to the damaged tissue.

Tubes containing cytokines or growth factors are particularly suited for sustained administration of cytokines or growth factors, as in the case of wound healing promotion. Osteoinductive factors and cofactors (including TGF-β) may advantageously be incorporated into compositions destined for bone repair. Tubes may be used to wrap transplanted organs, to suppress rejection and induce improved tissue growth. Alternatively, one may administer antiviral and antitumor factors such as TNF, interferons, CSFs, TGF-β, and the like for their pharmaceutical activities. The amount of cytokine or other pharmaceutically active drug incorporated in the tubes will depend upon the severity of the condition being treated, the rate of delivery desired, and the like. However, these parameters may easily be determined by routine experimentation, for example, by preparing a model composition following the examples below, forming a tubes therewith and assaying the release rate in a suitable animal model.

EXAMPLES

The following examples are put forth so as to provide those of ordinary skill in the art with a complete disclosure and description of how to make the conjugates and formulations used to produce the tubes and are not intended to limit the scope of what the inventors regard as their invention. Efforts have been made to ensure accuracy with respect to numbers used (e.g. amounts, temperature, molecular weight, etc.) but some experimental errors and deviation should be accounted for. Unless indicated otherwise, parts are parts by weight, molecular weight is average molecular weight, temperature is in degrees Centigrade, and pressure is at or near atmospheric.

EXAMPLE 1

Preparation of Collagen-PEG (A) Monomethyl-PEG 5000 (50 g, 10 mmol, Aldrich Chemical Co.) is dissolved in 1,2-dichoroethane 250 ml) and heated at reflux with glutaric anhydride (5 g) and pyridine (4 ml) under nitrogen for 3 days. The solution is then filtered and the solvent evaporated, and the residue dissolved in water (100 ml) and washed with diethyl ether (2X 50 ml). The resulting PEG-glutarate is extracted from the water with chloroform (2X 50 ml), and the chloroform evaporated to yield about 43 g of PEG-glutarate. The PEG-glutarate is then dissolved in dimethylformamide (DMF, 200 ml) at 37° C., and N-hydroxysuccinimide (10% molar xs) added. The solution is cooled to 0° C., and an equivalent amount of dicyclohexylcarbodiimide added in DMF solution (10 ml). The mixture is left at room temperature for 24 hours, and then filtered. Cold benzene (100 ml) is then added, and the PEG-succinimidyl glutarate (SG-PEG) precipitated by adding petroleum ether (200 ml) at 0° C. The precipitate is collected on a sintered glass filter. Dissolution in benzene, followed by precipitation with petroleum ether is repeated three times to provide "activated" PEG (SG-PEG).

Vitrogen 100 ® collagen in solution (400 ml, 1.2 g collagen, 0.004 mmol) was mixed with 0.2M phosphate buffer (44 ml) to elevate the pH to 7.4. Next, a threefold molar excess of SG-PEG (6.00 g, 1.2 mmol) was dissolved in water for injection (40 ml) and sterile-filtered. The SG-PEG solution was then added to the collagen solution, and the mixture allowed to stand at 17°-22° C. for about 15 hours. The solution was then centrifuged, and the resulting pellet (25 g) of reconstituted fibrils collected and washed with phosphate-buffered saline (PBS, 3X 400 ml) to remove residual PEG. The resulting material has a solid, coherent elasticity, and may be picked up on a spatula (the equivalent non-conjugated collagen, Zyderm ® Collagen Implant is more fluid). The resulting material may be extruded or diluted with a sufficient amount of a carrier to allow for the material to be extruded through a nozzle to form a tube. The tube may be dried in order to dehydrate the tube for storage.

(B) Similarly, proceeding as in part (A) above but substituting polypropylene glycol and POE-POP block polymers for polyethylene glycol, the corresponding collagen-PPG and collagen-POE-POP compositions are prepared. The compositions may be extruded with or without a diluting carrier to form a tube which is then dehydrated.

(C) Difunctionally activated PEG is prepared by dissolving PEG 3400 (34 g, 10 mmol, Aldrich Chemical Co.) in 1,2-dichoroethane (250 ml) and heated at reflux with glutaric anhydride (10 g) and pyridine (4 ml) under nitrogen for 3 days. The solution is then filtered and the solvent evaporated, and the residue dissolved in water (100 ml) and washed with diethyl ether (2X 50 ml). The resulting PEG-diglutarate is extracted from the water with chloroform (2X 50 ml), and the chloroform evaporated to yield PEG-diglutarate. The PEG-diglutarate is then dissolved in DMF (200 ml) at 37° C., and N-hydroxysuccinimide (10% molar xs) added. The solution is cooled to 0° C., and an equivalent amount of dicyclohexylcarbodiimide added in DMF solution (10 ml). The mixture is left at room temperature for 24 hours, and then filtered. Cold benzene (100 ml) is then added, and the PEG-di(succinimidyl glutarate) (dSG-PEG) precipitated by adding petroleum ether (200 ml) at 0° C. The precipitate is collected on a sintered glass filter. Dissolution in benzene, followed by precipitation with petroleum ether is repeated three times to provide difunctionally "activated" dPEG (dPEG*).

Vitrogen 100® collagen in solution (400 Ml, 1.2 g collagen, 0.004 mmol) was mixed with 0.2M phosphate buffer (44 ml) to elevate the Ph to 7.4. Next, a three-fold molar excess of dPEG* (6.00 g, 1.2 mmol) was dissolved in water for injection (40 ml) and sterile-filtered. The dPEG* solution was then added to the collagen solution, agitated, and the mixture allowed to stand at 17°-22° C. for about 15 hours. The solution was then centrifuged, and the resulting pellet of reconstituted fibrils collected and washed with PBS (3X 400 ml) to remove residual dPEG*. The pellet was then placed in a syringe fitted with a Luer lock hub connected to a second syringe, and was passed between the syringes until homogeneous. The resulting material is a microgel or a particulate suspension of random size fibrils in solution (microgel conjugate). The material is a smooth, pliable, rubbery mass, with a shiny appearance. The material may be formed into a tube in any appropriate manner and may be diluted, extruded and dried.

EXAMPLE 2

Characterization (A) Collagen-mPEG prepared in Example 1A was characterized and compared with Zyderm® collagen implant (ZCI), and glutaraldehyde-crosslinked fibrillar collagen (GAX).

Extrusion:

Tests were carried out to measure the force required to extrude the test composition through a 30 gauge needle. The force required was graphed (in Newtons) versus plunger travel, and ZCI was shown to be extruded smoothly, requiring a force of about 20-30 Newtons. GAX was not extruded smoothly, as shown by a "spiking" exhibited in the force trace. At the plateau, GAX required about 10-15 N for extrusion. In contrast, collagen-mPEG demonstrated a very low extrusion force (8-10 N), with little or no spiking.

Intrusion:

Intrusion is a measure of the tendency of a composition to "finger" or channel into a porous bed, rather than remaining in a compact mass. Low intrusion is preferred in augmentation of soft tissue, so that the injected tube does not dissolve and diffuse through the dermis and remains in place.

A 1 ml syringe fitted with a 30 gauge needle was half-filled with silicon carbide particles (60 mesh), simulating human dermis. The upper half of the syringe was filled with 0.5 ml test composition (GAX, ZCI, or collagen-mPEG) at 35 mg/ml. The plunger was then fitted, and depressed. On depression, ZCI appeared at the needle, demonstrating intrusion through the silicon carbide bed. Syringes filled with GAX or collagen-mPEG of the invention did not pass collagen, instead releasing only buffer, demonstrating no intrudability.

Helicity:

The portion of each composition exhibiting nonhelical character was measured using sensitivity to digestion with trypsin. Samples were treated with the protease trypsin, which is capable of attacking only fragmented portions of the collagen protein. The extent of hydrolysis is measured by fluorescamine assay for solubilized peptides, and the results are expressed as percentage non-helical collagen. The percentage of non-helical collagen was measured 30 minutes after the beginning of the digestion period. The results indicated that ZCI was 3-10% sensitive, GAX was 1-2% sensitive, and collagen-mPEG was about 1% sensitive. Sensitivity to trypsin may also correlate to sensitivity to endogenous proteases following implantation.

Collagenase Sensitivity:

The sensitivity of each composition to collagenase was also measured. ZCI was 65.2% digested, compared to 2.2% for GAX, and 45.8% for collagen-mPEG.

Phase Transition:

The behavior of each composition versus temperature was examined using a differential scanning calorimeter. On heating, ZCI exhibited multiple peaks at about 45° and 53° C. GAX exhibited a peak at 67°-70° C. Collagen-mPEG exhibited a peak at 56°-61° C.

Lysine Content:

The number of free lysines per mole was determined for each composition using TNBS to quantify reactive epsilon amino groups. ZCI exhibited about 30 lysines per (single helix) molecule (K/m), whereas GAX exhibited 26-27 K/m, and collagen-MPEG 21-26 K/m.

(B) Characterization of Crosslinked Collagen-Polymer Conjugates:

A collagen-dPEG conjugate prepared as described in Example 1C was characterized using differential scanning calorimetry (DSC). This test is a measure of the transition temperature during fragmentation of the collagen molecule at a microscopic level. A lowering of the transition temperature indicates an increase in fragmentation in a manner similar to that measured by trypsin sensitivity.

The collagen-dPEG conjugate showed a single denaturational transition at 56° C. by DSC, which is similar to the typical melting point of the collagen-PEG conjugate prepared in Example 1A. In comparison, ZCI has a melting temperature of 45°-53° C. with multiple denaturational transitions, and GAX has a melting temperature of 67°-70° C. with a single denaturational transition.

The extrusion test described in Example 2A could not be used to characterize the collagen-dPEG conjugate because the material was not extrudable through a 30 gauge needle.

Using the intrusion test described in Example 2A, the passage of collagen-dPEG was completely blocked at the silicon carbide bed, which indicates high crosslinking between the collagen molecules and little or no intrudability.

EXAMPLE 3

Immunogenicity

Noncrosslinked PEG-Collagen:

This experiment was conducted to demonstrate the relative immunogenicity of a collagen-mPEG preparation versus a commercially-available bovine collagen formulation prepared from essentially the same source material, and having a similar consistency. As both collagen preparations were prepared using atelopeptide collagen (which is only weakly immunogenic), the preparations were formulated with either complete Freund's adjuvant (CFA) or incomplete Freund's adjuvant (IFA), to enhance the immune response. This is a severe test, designed to magnify any possible immune reaction.

Collagen-mPEG was prepared as in Example 1A above. Male Hartley guinea pigs (11) were anesthetized and bled by heart puncture for pre-immunization serologic evaluation. Five animals were treated with two 0.1 ml intramuscular injections of Zyderm® Collagen Implant (ZCI) emulsified in CFA (1:9) in the left and right thighs. Another five animals were treated in the same fashion, using collagen-PEG (35 mg/ml) emulsified in CFA. One animal was treated with collagen-PEG in IFA. At day 14 following immunization, all animals were again bled by heart puncture, and serum obtained for antibody titer determination (using ELISA). Serology was again performed at day 30.

On day 30, following collection of serum samples, each animal was challenged intradermally with both ZCI and collagen-PEG (0.1 ml of each, one on each flank). Delayed-type hypersensitivity (DTH) was quantified as a measure of cell-mediated immunity. DTH was evaluated at 24, 48, and 72 hours post-challenge by measuring the diameter of any wheal using micrometer calipers, and noting the extent of erythema and induration. Animals were then euthanized with $CO_2$, and the injection sites excised and fixed in neutral, buffered formalin for histological study.

Serological results indicated reduced immunogenicity of collagen-PEG versus ZCI. At day 14, 80% of ZCI immunized animals exhibited "positive" antibody responses (titer≧160 at day 14), whereas 0% of the collagen-PEG immunized animals exhibited positive responses. At day 30, all ZCI-immunized animals exhibited high antibody titers, whereas none of the collagen-PEG-immunized animals (C-PEG) exhibited high titers. The data are shown in Table 1.

TABLE 1

| | | Immunogenicity | |
|---|---|---|---|
| | | Antibody Titer | |
| Animal | Treatment | day 14 | day 30 |
| 1 | ZCI | 320 | >2560 |
| 2 | ZCI | 320 | 1280 |
| 3 | ZCI | 2560 | >2560 |
| 4 | ZCI | 320 | >2560 |
| 5 | ZCI | 80 | 2560 |
| 6 | C-PEG | 0 | 0 |
| 7 | C-PEG | 0 | 160 |
| 8 | C-PEG | 40 | 640 |
| 9 | C-PEG | 0 | 20 |
| 10 | C-PEG | 0 | 640 |
| 11 | C-PEG (IFA) | 0 | 160 |

Responses to the DTH challenge also demonstrated that the collagen-mPEG of the invention is less immunogenic. Guinea pigs immunized with ZCI and challenged with ZCI exhibited a wheal measuring 1.128±0.058 cm in diameter. Animals immunized with collagen-mPEG and challenged with collagen-mPEG exhibited wheals measuring 0.768±0.036 cm. Animals immunized with ZCI and challenged with collagen-mPEG, or immunized with collagen-mPEG and challenged with ZCI, developed wheals smaller than the ZCI-immunized ZCI-challenged wheals. Responses measured at 48 and 72 hours were essentially the same or lower than the 24 hour response for each site. Erythema was essentially the same for all animals.

Histological studies showed that both materials exhibited comparable intrusion, fingering into the dermis and subcutaneous space. Sites of intradermal challenge with ZCI in ZCI-immunized animals exhibited the most extensive inflammatory response, including a cellular infiltrate of lymphohistiocytic elements with eosinophils and occasional giant cells. Two of the implant sites demonstrated an erosive inflammation of the overlying epidermis and eschar formation. Sites of intradermal challenge with collagen-mPEG in ZCI-immunized animals exhibited only a moderate associated inflammatory infiltrate, with a marked reduction in acute cells and lymphoid elements. Histiocytes and giant cells were more prevalent, and in some samples lined and colonized the implants heavily. Animals immunized with collagen-mPEG exhibited only slight to moderate reaction, with ZCI challenge sites accompanied by a modest lymphohistiocytic perivascular infiltrate with a few eosinophils and giant cells. Collagen-mPEG challenge sites were typically accompanied by a minimal scattering of lymphoid cells near the associated vasculature.

EXAMPLE 4 In situ Crosslinking

A DPEG solution was prepared as described in Example 1C above. The following samples were then prepared:

(1) 5 mg DPEG in 80 μL water, mixed with 0.5 mL fibrillar collagen (35 mg/mL), to a final DPEG concentration of 1% by volume;

(2) 15 mg DPEG in 80 μL water, mixed with 0.5 mL fibrillar collagen (35 mg/mL), to a final DPEG concentration of 3% by volume;

(3) Vitrogen® 100 collagen in solution;

(4) 5 mg DPEG in 80 μL water, mixed with 0.5 mL non-fibrillar collagen (35 mg/mL), to a final DPEG concentration of 1% by volume;

(5) 15 mg DPEG in 80 μL water, mixed with 0.5 mL non-fibrillar collagen (35 mg/mL), to a final dPEG concentration of 3% by volume;

(6) 5 mg dPEG in 0.5 mL PBS, to a final dPEG concentration of 1% by volume; and (7) GAX.

The dPEG solutions of Samples 1, 2, 4, and 5 were placed in a 1 mL syringe equipped with a Luer lock fitting and connector, and joined to another syringe containing the collagen material. The solutions were mixed by passing the liquids back and forth between the syringes several times to form the homogeneous reaction mixture.

The syringe connector was then removed and replaced with a 27 gauge needle, and approximately 50 μL of the reaction mixture was injected intradermally into each of 20 guinea pigs. Samples 3, 6, and 7 were similarly administered through a 27 gauge needle. At intervals up to 30 days following injection, the treatment sites were harvested and studied histologically.

By 30 days, all of the materials appeared to be biocompatible. Samples 1 and 2 displayed wide dispersion with an intermediate degree of interdigitation with dermal collagen fibers. Colonization by connective tissue cells was moderate, and a trace of round cell infiltrate with eosinophils was seen.

Samples 3, 4 and 5 were highly dispersed and finely interdigitated with dermal collagen fibers. Colonization was mild to moderate, and trace levels of round cell infiltration were seen.

Sample 6 had no detectable effects. Sample 7 occurred as large islands with moderate colonization and trace to mild levels of inflammation.

EXAMPLE 5

Collagen-Polymer-Growth Factor Conjugates (A) A conjugate containing crosslinked collagen-dPEG-TGF-$\beta 2$ was prepared as follows:

A solution of TGF-$\beta 2$ and $^{125}$I-TGF-$\beta 2$ ($10^5$ cpm; 25 $\mu$L of 1 mg/mL) was added to a solution of dPEG* (4 mg) in $CH_2Cl_2$ (100 $\mu$L), and the mixture allowed to react for 12 (sample #3) or 35 (sample #5) minutes at 17° C. To this was added 2.5 mL of collagen solution (3 mg/mL atelopeptide nonfibrillar collagen), and the resulting mixture allowed to incubate overnight at ambient temperature. The pellet which formed was collected by centrifugation to provide collagen-dPEG-TGF-$\beta 2$.

(B) A composition based on fibrillar atelopeptide collagen was prepared as in part A above, but limiting TGF-$\beta 2$/dPEG* reaction time to 2 minutes, and substituting 7 mg of fibrillar collagen (precipitated from collagen in solution within 2 minutes prior to use) for collagen in solution.

(C) A composition containing dPEG-crosslinked collagen and free TGF-$\beta 2$ was prepared as follows:

A solution of dPEG* (4 mg) in $CH_2Cl_2$ (100 $\mu$L), was added to 2.5 mL of CIS (3 mg/mL atelopeptide nonfibrillar collagen), and the resulting mixture allowed to incubate overnight at ambient temperature. The pellet which formed was washed to remove unreacted dPEG*, and 25 $\mu$g of TGF-$\beta 2$ mixed in to provide collagen-dPEG+TGF-$\beta 2$.

(D) The degree of TGF-$\beta 2$ binding was determined as follows:

Each composition prepared in parts A–C above was washed six times with 0.5 mL of buffer (0.02M phosphate buffer, 0.1% BSA) by vigorous vortexing followed by centrifugation in order to remove non-bound TGF-$\beta 2$. The pellet and supernatants were collected at each time of washing, and were counted. The TGF-$\beta 2$ in the simple mixture is quantitatively released within about 6 washings, while approximately 40% of the TGF-$\beta 2$ is retained in the compositions of part B and 50% is retained in the compositions of part A.

(E) The biological activity of the materials prepared above was assayed as follows:

Compositions prepared according to part A (CIS-dPEG-TGF-$\beta 2$) (TGF-$\beta 2$/dPEG* reaction time of 12 minutes) and part C (CIS-dPEG+TGF-$\beta 2$) were prepared, as well as a control prepared according to part C without TGF-$\beta 2$ (CIS-dPEG). The samples were washed in PBS/BSA eight times then washed an additional three times in fetal bovine serum (Gibco) at 37° C. This washing protocol resulted in visually detectable material loss, so remaining TGF-$\beta 2$ content was determined by counting the remaining $^{125}$I. TGF-$\beta 2$ activity was then assayed by ELISA. The results are shown in Table 2 below.

TABLE 2

| | Retention of Biological Activity | | |
|---|---|---|---|
| Sample | $^{125}$I Counts | remaining TGF-$\beta 2(\mu g)$ | O.D. (414 nm) |
| CIS-dPEG | 0 | 0 | 0.015 |
| | | | 0.015 |
| CIS-dPEG + TGF-$\beta 2$ | 2775 | 0.5–1.0 | 0.029 |
| | | | 0.035 |
| CIS-dPEG-TGF-$\beta 2$ | 42604 | 7.4 | 0.102 |
| | | | 0.082 |

The data demonstrates that the TGF-$\beta 1$ retained in the compositions of the invention remains in a substantially active form.

EXAMPLE 6

Formulations (A) A formulation suitable for extrusion were prepared by suspending collagen-PEG in sterile water for injection, at 35 mg/mL. The characteristics of the resulting formulation are described in Example 2 above.

(B) A formulation useful for repair of stress-bearing bone defects (e.g., fractures, nonunions, and the like) may be prepared by mixing collagen-PEG of the invention with a suitable particulate, insoluble component. The insoluble component may be fibrillar crosslinked collagen, gelatin beads, polytetrafluoroethylene beads, silicone rubber beads, hydrogel beads, silicon carbide beads, mineral beads, or glass beads, and is preferably a calcium mineral, for example hydroxyapatite and/or tricalcium phosphate.

Solid formulations were prepared by mixing Zyderm®II (65 mg/mL collagen) or collagen-mPEG (63 mg/mL) with particulate hydroxyapatite and tricalcium phosphate (HA+TCP) and air drying to form a solid block containing 65% HA by weight. Optionally, blocks were heat-treated by heating at 75° C. for 10 hours. The resulting blocks were hydrated in 0.13M saline for 12 hours prior to testing.

On standing, it was observed that Zyderm®-HA+TCP (Z-HA) compositions separated into three phases, whereas PEG-collagen-HA+TCP (PC-HA) compositions remained single phase.

Each block was elongated by 5%, after its stress relaxation monitored for 1 minute after release. After this test, each block was subjected to constant elongation at a constant 1 cm/min until failure. The results are shown in Table 3:

TABLE 3

| | Mechanical Strength | | | | |
|---|---|---|---|---|---|
| | Stress Relaxation | | | Constant Extension | |
| Sample | Peak Force | Constant Force | $t_{\frac{1}{2}}$ (min) | Rupture Force | Extension at Rupture |
| Z-HA | 1.5 | 1.1 | 0.04 | 2.6 | 11.0% |
| (air) | — | — | — | 2.6 | 15.3% |
| Z-HA | 1.5 | 1.1 | 0.06 | — | — |
| (heat) | 1.4 | 1.0 | 0.07 | 3.4 | 14.0% |
| PC-HA | 2.6 | 1.8 | 0.06 | 5.5 | 12.3% |
| (air) | 2.8 | 2.1 | 0.08 | 5.4 | 11.7% |
| PC-HA | 3.3 | 2.6 | 0.04 | 5.4 | 12.0% |
| (heat) | 3.6 | 2.7 | 0.06 | 5.4 | 20.3% |

All forces reported in newtons. Extension at rupture (strain) reported in percent extension.

The data demonstrate that collagen-polymer forms HA+TCP compositions exhibiting substantially greater tensile strength. Thus, one can prepare implant compositions with collagen-polymer which are substantially stronger than compositions employing the same amount of non-conjugated collagen, or may reduce the amount of collagen-polymer employed to form a composition of equal strength.

EXAMPLE 7

Zyderm®I Collagen (35 mg/ml) and Zyderm®II Collagen (65 mg/ml) (both available from Collagen Corporation, Palo Alto, Calif.) were crosslinked using difunctional SG-PEG and formed into disks. The disks were dehydrated and later rehydrated. Diameter, thickness and weight of the disks were measured in the fresh (wet), dehydrated, and rehydrated states. Results of these measurements are presented in Table 4, below.

TABLE 4

Swellability of Collagen Disks (35 and 65 mg/ml) Crosslinked by dSG-PEG

| Sample* | Diameter (mm) | | | Thickness (mm) | | | Weight (grams) | | |
|---|---|---|---|---|---|---|---|---|---|
| | Fresh | Dehyd. | Rehyd. | Fresh | Dehyd. | Rehyd. | Fresh | Dehyd. | Rehyd. |
| Z-I + PEG | 14 | 12 | 13.1 | 2.0 | 0.6 | 1.9 | 0.3213 | 0.0215 | 0.3048 |
| Z-II + PEG | 14 | 10 | 13.7 | 2.0 | 1.0 | 1.8 | 0.4111 | 0.0385 | 0.3943 |

Z-I = Zyderm ® Collagen
Z-II = Zyderm ® Collagen

The crosslinked collagen disks (at both collagen concentrations) regained nearly all of their original dimensions upon rehydration.

EXAMPLE 8

Preparation of Smooth Collagen-Polymer Tube

The needle end was snipped off of a standard 4.5 mm inner diameter syringe containing Zyderm ®I Collagen (35 mg/ml, available from Collagen Corporation, Palo Alto, Calif.). Using the syringe plunger, the collagen was pushed out of the cut syringe in a solid cylinder. The collagen cylinder was placed in a petri dish and immersed in a 10% solution of difunctional S-PEG (1.0 g of difunctional S-PEG in 10 ml of PBS).

The collagen cylinder was allowed to incubate in the 10% S-PEG solution at room temperature. The crosslinking reaction occurs as the PEG diffuses from the outside towards the inside of the collagen cylinder. After 20-30 minutes of incubation in the S-PEG solution, the outside of the collagen cylinder had been crosslinked, while the inside remained non-crosslinked.

After 20-30 minutes of incubation, the collagen cylinder was removed from the crosslinker solution. The inner, non-crosslinked collagen could easily be squeezed out from the outer crosslinked shell using manual pressure, leaving a hollow tube of PEG-crosslinked collagen.

The hollow tube was then returned to the 10% S-PEG solution and incubated overnight at 37° C. in order to complete the crosslinking process.

The outer diameter of the hollow PEG-collagen tube can be varied by varying the size of the collagen cylinder starting material. The inner diameter of the tube can be increased by decreasing the length of time for the initial incubation of the collagen cylinder in the PEG solution. Conversely, the inner diameter of the tub can be made smaller by increasing the initial incubation period.

EXAMPLE 9

Preparation of Pleated Collagen-Polymer Tube

A smooth collagen-polymer tube was prepared according to the method described in Example 8. While still wet, the tube was slipped over the plunger of the same syringe that had originally contained the Zyderm ® I Collagen starting material. The tube fit snugly over the syringe plunger. The PEG-collagen tube was then pushed down along the axis of the syringe plunger, forming pleats or ribs in the wet tubing, so that the pleated tube was now approximately half the length of the original smooth tube.

While still on the syringe plunger, the pleated PEG-collagen tube was dried under the fume hood at room temperature. After 24 hours, the dried pleated tube was pushed off the syringe plunger. The tube retained its pleated shape after removal from the syringe plunger.

The pleated PEG-collagen tube was then placed in a petri dish containing water. The tube retained its pleated shape following rehydration.

EXAMPLE 10

Preparation of Small Diameter Pleated Collagen-Polymer Tubing 0.9 cc of Zyderm ® I Collagen was mixed with 0.1 cc of 5% solution of difunctional S-PEG (5 mg of S-PEG in 0.1 cc of PBS) using syringe-to-syringe mixing. Immediately following mixing, the PEG-collagen material was extruded using an 18-gauge needle into TFE tubing (1.5 mm outer diameter, 1.3 mm inner diameter). (It was necessary to add a certain amount of PEG to provide a starting material with greater structural integrity than straight Zyderm ® I Collagen in order to maintain the shape of the small-diameter cylinder.)

After 20-30 minutes of incubation at room temperature, the tubing was sliced open and the solid cylinder of PEG-collagen was peeled out of the tubing. The PEG-collagen cylinder was then placed in a petri dish containing 5 cc of 10% solution of difunctional S-PEG. The crosslinking reaction occurs as the PEG diffuses from the outside towards the inside of the collagen cylinder. After 3 hours of incubation in the S-PEG solution at room temperature, the inside of the cylinder was pushed out using a 1-mm diameter mandrel, resulting in a hollow, smooth PEG-collagen tube.

The PEG-collagen tube was then pushed down along the axis of the mandrel, forming pleats or ribs in the wet tubing, so that the pleated tube was now approximately half the length of the original smooth tube.

While still on the mandrel, the pleated PEG-collagen tube was dried under the fume hood at room temperature. After 24 hours, the dried pleated tube was pushed off the mandrel. The tube retained its pleated shaped after removal from the mandrel.

The pleated PEG-collagen tube was then placed in a petri dish containing water. The tube retained its pleated shape following rehydration.

PEG-collagen tubes of different diameters can be prepared by using different sizes of the TFE tubing and varying the time for the crosslinking reaction to occur.

EXAMPLE 11

Preparation of Thin-Walled Tubes 0.90 ml of Zyderm ®I Collagen was mixed with a solution of 10 mg of difunctional S-PEG in 0.10 ml of PBS using syringe-to-syringe mixing.

A TFE tube having an inner diameter of 0.9 mm was placed inside another TFE tube having an inner diameter of 1.2 mm. The PEG-collagen mixture was injected through a 27-gauge needle into the space between the inner and outer tubes. The tubing was then incubated at 37° C. for 2 hours.

The outer tubing was pulled off and the inner tubing with the PEG-collagen shell around it was incubated at 37° C. for an additional 2 hours.

The thin PEG-collagen shell was then carefully pushed off of the inner TFE tubing. The resulting PEG-collagen tube was clear and cellophane-like in consistency.

The PEG-collagen tube was then placed in water to rehydrate. Although the tube was very thin and had a small diameter, water could be injected through it.

The thickness of the tube wall and the inner diameter of the collagen-polymer tube can be varied by varying the size of the inner and outer TFE tubes used to mold the collagen-polymer material. Thin-walled tubes produced according to the method described above may be especially suited for use as nerve guide tubes to facilitate nerve regeneration.

The invention is shown and described herein at what is considered to be the most practical, and preferred embodiments. It is recognized, however, that departures may be made therefrom which are within the scope of the invention and that obvious modifications will occur to one skilled in the art upon reading this disclosure.

What is claimed:

1. A hollow, flexible tube having a circular cross-section, an outer diameter in the range of about 0.25 mm to about 5.0 cm, an inner diameter in the range of 0.05 mm to 4.95 cm, and a length of greater than 10 mm, the tube comprising collagen chemically conjugated to a synthetic non-immunogenic hydrophilic polymer by a covalent bond wherein the covalent bond is selected from the group consisting of an ester linkage, a urethane linkage, and an ether linkage.

2. The tube of claim 1, wherein the tube is dehydrated.

3. The tube of claim 1, wherein the synthetic hydrophilic polymer is a difunctionally activated polyethylene glycol.

4. The tube of claim 1, wherein the polymer is difunctional polyethylene glycol succinimidyl.

5. The tube of claim 1, further comprising:
a therapeutically effective amount of a cytokine or growth factor.

6. The tube of claim 5, wherein said cytokine or growth factor is selected from the group consisting of epidermal growth factor, transforming growth factor-α, transforming growth factor-β, transforming growth factor-β2, platelet-derived growth factor-AA, platelet-derived growth factor-AB, platelet-derived growth factor-BB, acidic fibroblast growth factor, basic fibroblast growth factor, connective tissue activating peptide, β-thromboglobulin, insulin-like growth factors, tumor necrosis factor, interleukins, colony stimulating factors, erythropoietin, nerve growth factor, interferons, and osteogenic factors.

7. The tube of claim 6, wherein said growth factor is selected from the group consisting of transforming growth factor-β, transforming growth factor-β1, transforming growth factor-β2, and erythropoietin.

8. The tube of claim 1, wherein the synthetic hydrophilic polymer is a succinimidyl monomethylpolyethylene glycol glutarate.

9. The tube of claim 1, wherein the conjugate has the following general structural formula:

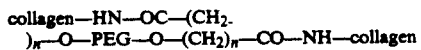

wherein n is an integer selected from the group consisting of 0, 1, 2, 3, or 4.

10. The tube of claim 1, wherein the collagen is selected from the group consisting of type I, type II and type III collagen and the polymer is polyethylene glycol having a weight average molecular weight of about 100 to about 20,000.

11. The tube of claim 10, wherein said synthetic hydrophilic polymer is bound to an available lysine residue on said collagen.

12. The tube of claim 10, wherein said collagen is atelopeptide fibrillar collagen.

13. The tube of claim 1, wherein the covalent bond is an ether linkage.

14. A method of repairing a channel in a mammal comprising attaching to a channel in need of repair a tube having an outer diameter in the range of about 0.25 mm to about 5.0 cm, and a length of more than 5 mm, the tube being comprised of collagen chemically conjugated to a synthetic non-immunogenic hydrophilic polymer by a covalent bond wherein the covalent bond is selected from the group consisting of an ester linkage, a urethane linkage, and an ether linkage.

15. The method of claim 14, further comprising:
hydrating the tube by placing the tube in contact with an aqueous solution prior to attaching the tube to the channel.

16. The method of claim 15, wherein the synthetic, hydrophilic, non-immunogenic polymer has the following structural formula:

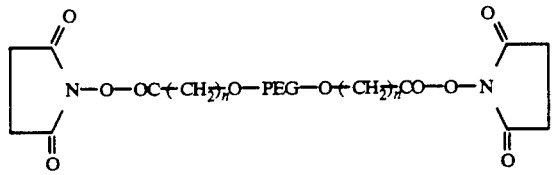

wherein n is selected from the group consisting of 0, 1, 2, 3 and 4.

17. The method of claim 15, wherein the synthetic, hydrophilic, non-immunogenic polymer has the following structural formula:

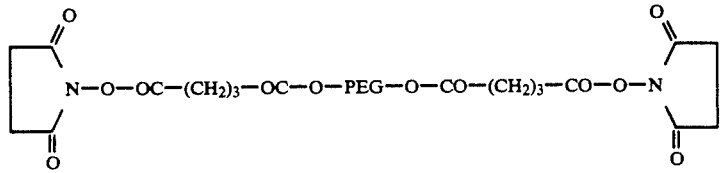

18. The method of claim 15, wherein the synthetic, hydrophilic, non-immunogenic polymer has the following structural formula:

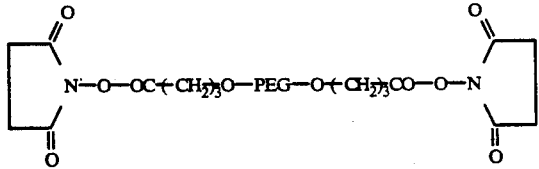

19. The method of claim 15, wherein the synthetic, hydrophilic, non-immunogenic polymer has the following structural formula:

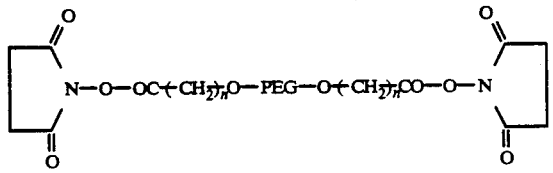

wherein n is selected from the group consisting of 0, 1, 2, 3 and 4.

20. The method of claim 15, wherein the mammal is a human and the channel is selected from the group consisting of a vein, artery, intestine, fallopian tube, vas deferens, urethra, esophagus and trachea.

21. The method of claim 14, wherein the covalent bond is an ether linkage.

22. A method of repairing a channel in a mammal comprising:

placing a tube in a channel in need of repair, wherein the tube has an outer diameter in the range of about 0.25 mm to about 5.0 cm, and a length of more than 2 cm, the tube being comprised of collagen chemically conjugated to a synthetic, non-immunogenic, hydrophilic polymer by a covalent bond wherein the covalent bond is selected from the group consisting of an ester linkage, a urethane linkage, and an ether linkage.

23. The method of claim 22, wherein the covalent bond is an ether linkage.

* * * * *